US005708034A

United States Patent [19]
Kleemann et al.

[11] Patent Number: 5,708,034
[45] Date of Patent: Jan. 13, 1998

[54] SUBSTITUTED SULFONIMIDAMIDES, PROCESSES FOR THEIR PREPARATION, THEIR USE AS A MEDICAMENT OR DIAGNOSTIC, AND MEDICAMENT COMPRISING THEM

[75] Inventors: Heinz-Werner Kleemann, Bischofsheim; Joachim Brendel, Bad Vilbel; Jan-Robert Schwark, Frankfurt; Andreas Weichert, Egelsbach; Hans Jochen Lang, Hofheim; Udo Albus, Florstadt; Wolfgang Scholz, Eschborn, all of Germany

[73] Assignee: Hoechst Aktiengesellschaft, Frankfurt am Main, Germany

[21] Appl. No.: 740,634

[22] Filed: Oct. 31, 1996

[30] Foreign Application Priority Data

Nov. 3, 1995 [DE] Germany ............... 195 40 995.7

[51] Int. Cl.$^6$ ............... A61K 31/275; A61K 31/21; A61K 31/18; A61K 31/165
[52] U.S. Cl. ............ 514/618; 514/506; 514/522; 514/579; 514/603; 514/607; 514/608; 514/616; 514/824; 514/825; 514/826; 514/851; 514/866; 514/893; 560/317; 558/413; 564/1; 564/85; 564/101; 564/102; 564/154; 564/162
[58] Field of Search ............... 514/506, 522, 514/579, 603, 607, 608, 616, 618, 824, 825, 826, 851, 866, 893; 560/317; 558/13; 564/1, 85, 101, 102, 154, 162

[56] References Cited

U.S. PATENT DOCUMENTS

| 3,780,027 | 12/1973 | Ciagoe, Jr. et al. | 260/239.6 |
|---|---|---|---|
| 5,091,394 | 2/1992 | Englert et al. | 514/331 |
| 5,140,039 | 8/1992 | DeBernardis et al. | 514/422 |
| 5,185,364 | 2/1993 | DeBernardis et al. | 514/444 |
| 5,292,755 | 3/1994 | Englert et al. | 514/331 |
| 5,364,868 | 11/1994 | Englert et al. | 514/331 |
| 5,373,024 | 12/1994 | Lang et al. | 514/618 |
| 5,395,826 | 3/1995 | Naumann et al. | 514/107 |
| 5,416,094 | 5/1995 | Lal et al. | 514/307 |
| 5,498,617 | 3/1996 | Naumann et al. | 514/315 |
| 5,516,805 | 5/1996 | Lang et al. | 514/620 |
| 5,547,953 | 8/1996 | Weichert et al. | 514/226.5 |
| 5,559,153 | 9/1996 | Schwark et al. | 514/597 |
| 5,567,734 | 10/1996 | Schwark et al. | 514/617 |
| 5,571,842 | 11/1996 | Kleemann et al. | 514/618 |
| 5,591,754 | 1/1997 | Lang et al. | 514/331 |

FOREIGN PATENT DOCUMENTS

| 3301493 | 8/1993 | Australia. |
|---|---|---|
| 5271693 | 12/1993 | Australia. |
| 4163593 | 1/1994 | Australia. |
| 5527994 | 2/1994 | Australia. |
| 5236893 | 6/1994 | Australia. |
| 5249093 | 6/1994 | Australia. |
| 5522994 | 8/1994 | Australia. |
| 6454394 | 12/1994 | Australia. |
| 6454494 | 12/1994 | Australia. |
| 4221896 | 2/1995 | Australia. |
| 6881194 | 2/1995 | Australia. |
| 6884494 | 2/1995 | Australia. |
| 7150794 | 3/1995 | Australia. |
| 1635495 | 10/1995 | Australia. |
| 1786195 | 11/1995 | Australia. |
| 2330095 | 1/1996 | Australia. |
| 3050495 | 3/1996 | Australia. |
| 3050595 | 3/1996 | Australia. |
| 3050605 | 3/1996 | Australia. |
| 3900895 | 5/1996 | Australia. |
| 2168315 | 1/1996 | Canada. |
| 0325964 | 8/1989 | European Pat. Off.. |
| 9426709 | 11/1994 | WIPO. |
| 9604241 | 2/1996 | WIPO. |

OTHER PUBLICATIONS

Duff, Henry J. et al., *Circulation*, 79(6), 1257–63 (1989).
Dixon, Robert P. et al., *J. Am Chem Soc.* (1992) 114(1), 365–6.
*Eur. Heart of J.* 9(suppl. 1):25 and 167 (1988) book of abstracts.
Schmid, Andreas et al. *Biochemical and Biophysical Research Comm.* 112–117 (1992).
Scholz, Wolfgang et al. *Cardiovascular Res.* (1995) 29(2):260–8.
Rosskopf, Dieter et al. *Cellular Physiology Biochem* (1995), (5)4, 269–275.
Scholz, Wolfgang et al. *Basic Research Cardiology* (1993), 88(5), 443–55.
Sack, Stefan et al. *J. Cardiovasc. Pharmacol.* (1994)23(1), 72–78.

(List continued on next page.)

Primary Examiner—Peter O'Sullivan
Attorney, Agent, or Firm—Finnegan, Henderson, Farabow, Garrett & Dunner, L.L.P.

[57] ABSTRACT

Substituted sulfonimidamides, processes for their preparation, their use as a medicament or diagnostic, and medicament comprising them Sulfonimidamides of the formula I $$\begin{array}{c} R1 \\ N{\diagup} \\ \| \\ O{=}S{-}R2 \\ | \\ N \\ {\diagup}\,{\diagdown} \\ R4 \quad R3 \end{array} \quad I$$

in which at least one of the three substituents R(1), R(2) and R(3) is a benzoylguanidine, and in which the other substituents have the meanings indicated in the claims, are outstandingly suitable as medicaments having action on the cardiovascular system; that is as antiarrhythmic pharmaceuticals having a cardioprotective component as well as for treating ischemically induced damage; also in operative interventions, such as organ transplantation.

28 Claims, No Drawings

OTHER PUBLICATIONS

Kranzhofer, Roger et al. *Circ. Res.* (1993), 73(2), 264–8.

Scholz, Wolfgang et al. *Br. J. Pharmacol.* (1993), 109(2), 562–8.

Scholz, Wolfgang et al. *J. Mol. Cell. Cardiol.* (1992) 24(7), 731–39.

Scholz, Wolfgang et al. *Cardiovascular Research.* (Feb., 1995) vol. 29(2), 184–8.

*Biological Chemistry* Hoppe–Seyler (1991), vol. 372, No. 9, p. 750.

Mitsuka, Masayuki et al. *Circulation Research* (1993), vol. 73(2):269–275.

SUBSTITUTED SULFONIMIDAMIDES, PROCESSES FOR THEIR PREPARATION, THEIR USE AS A MEDICAMENT OR DIAGNOSTIC, AND MEDICAMENT COMPRISING THEM

BACKGROUND OF THE INVENTION

The invention relates to sulfonimidamides of the formula I

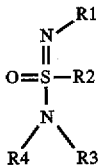

in which:
at least one of the three substituents R(1), R(2) and R(3) is a benzoylguanidine

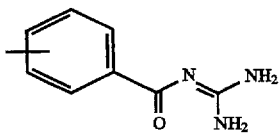

which is unsubstituted or substituted in the phenyl moiety by 1-4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27)N—SO$_2$, —OR(35), —SR(35) or —NR(35)R(36);

m is zero, 1 or 2;

R(14) is —(C$_3$–C$_8$)-cycloalkyl or phenyl, which is unsubstituted or substituted by 1-3 substituents selected from the group consisting of F and Cl, —CF$_3$, methyl, methoxy and —NR(15)R(16);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;

R(29) is —(C$_3$–C$_7$)-cycloalkyl or phenyl, which is unsubstituted or substituted by 1-3 substituents selected from the group consisting of F, Cl, —CF$_3$, methyl, methoxy and —NR(30)R(31);

R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24) and also R(26) and R(27) together are 5 or 6 methylene groups, of which a CH$_2$ group can be replaced by oxygen, —S—, —NH—, —NCH$_3$ or —N-benzyl;

R(35) and R(36) independently of one another are hydrogen or alkyl having 1, 2, 3, 4, 5 or 6 carbon atoms;

or

R(35) and R(36) together are 4-7 methylene groups, of which a CH$_2$ group can be replaced by oxygen, —S—, —NH—, —NCH$_3$ or —N-benzyl;

or

R(35) is phenyl, which is unsubstituted or substituted by 1-3 substituents selected from the group consisting of F, Cl, —CF$_3$, methyl, methoxy, SO$_2$R(5), SO$_2$NR(6)R(7) and —NR(32)R(33);

R(5) is alkyl having 1, 2, 3, 4, 5 or 6 carbon atoms

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms;

or

R(35) is C$_1$–C$_9$-heteroaryl, which is unsubstituted or substituted by 1-3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10)

p is zero, 1, 2, 3 or 4;

R(10) is phenyl, which is unsubstituted or substituted by 1-3 substituents selected from the group consisting of F, Cl, —CF$_3$, methyl, methoxy, —SO$_2$NR(17)R(8) and —SO$_2$R(9);

R(17) and R(8) independently of one another are hydrogen or alkyl having 1, 2, 3 or 4 carbon atoms;

R(9) is alkyl having 1, 2, 3 or 4 carbon atoms;

or the other radical R(1) and R(3) in each case is hydrogen, R(4) is hydrogen or alkyl having 1, 2, 3 or 4 carbon atoms; and their pharmaceutically tolerable salts.

Preferred compounds of the formula I are those in which: one of the substituents R(1), R(2) and R(3) is a benzoylguanidine

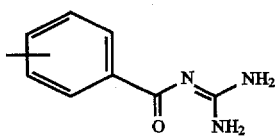

which is unsubstituted or substituted in the phenyl moiety by 1-3 substituents selected from the group consisting of alkyl having 1, 2, 3 or 4 carbon atoms, alkenyl having 2, 3 or 4 carbon atoms, —(CH$_2$)$_m$R(14), F, Cl, CF$_3$, R(22)SO$_2$—, R(23)R(24)N—CO—, R(25)—CO—, R(26)R(27)N—SO$_2$, —OR(35), —SR(35) and —NR(35)R(36);

R(22) and R(25) independently of one another are methyl or —CF$_3$;

R(23), R(24), R(26) and R(27) independently of one another are hydrogen or methyl;

m is zero, 1 or 2;

R(14) is —(C$_3$–C$_6$)-cycloalkyl or phenyl, which is unsubstituted or substituted by 1-2 substituents selected from the group consisting of F and Cl, —CF$_3$, methyl and methoxy R(35) and R(36) independently of one another are hydrogen or alkyl having 1, 2, 3 or 4 carbon atoms;

or

R(35) and R(36) together are 4-6 methylene groups, of which a CH$_2$ group can be replaced by oxygen, —S—, —NH— or —NCH$_3$;

or

R(35) is phenyl, which is unsubstituted or substituted by 1-2 substituents selected from the group consisting of F, Cl, —CF$_3$, methyl, methoxy, SO$_2$R(5) and SO$_2$NR(6)R(7)

R(5) is alkyl having 1, 2, 3 or 4 carbon atoms

R(6) and R(7) independently of one another are hydrogen, methyl or ethyl;

or

R(35) is $C_1$–$C_9$-heteroaryl, which is unsubstituted or substituted by 1–2 substituents selected from the group consisting of F, Cl, $CF_3$, $CH_3$ and methoxy;

and the other substituents R(1), R(2) and R(3) in each case independently of one another are alkyl having 1, 2, 3, 4, 5 or 6 carbon atoms or $(CH_2)_p R(10)$ p is zero, 1 or 2;

R(10) is phenyl, which is unsubstituted or substituted by 1–2 substituents selected from the group consisting of F, Cl, $CF_3$, methyl, methoxy, —$SO_2NR(17)R(8)$ and —$SO_2R(9)$;

R(17) and R(8) independently of one another are hydrogen, methyl or ethyl;

R(9) is methyl or ethyl;

or the other substituent R(1) and R(3) in each case is hydrogen,

R(4) is hydrogen or alkyl having 1, 2, 3 or 4 carbon atoms; and their pharmaceutically tolerable salts.

Particularly preferred compounds of the formula I are those in which: one of the substituents R(1), R(2) and R(3) is a benzoylguanidine

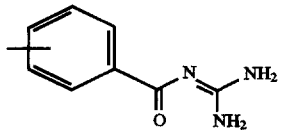

which is unsubstituted or substituted in the phenyl moiety by 1–2 radicals selected from the group consisting of alkyl having 1, 2, 3 or 4 carbon atoms, R(14), F, Cl, $CF_3$, R(22)$SO_2$—, R(23)R(24)N—CO—, R(25)—CO—, R(26)R(27)N—$SO_2$, —OR(35), —SR(35) and —NR(35)R(36);

R(22) and R(25) independently of one another are methyl or $CF_3$;

R(23), R(24), R(26) and R(27) independently of one another are hydrogen or methyl;

R(14) is —($C_3$–$C_6$)-cycloalkyl or phenyl, which is unsubstituted or substituted by a substituent selected from the group consisting of F and Cl, —$CF_3$, methyl and methoxy;

R(35) and R(36) independently of one another are hydrogen or alkyl having 1, 2, 3 or 4 carbon atoms;

or

R(35) is phenyl, which is unsubstituted or substituted by a substituent selected from the group consisting of F, Cl, —$CF_3$, methyl, methoxy, $SO_2CH_3$ and $SO_2NR(6)R(7)$;

R(6) and R(7) independently of one another are hydrogen, methyl or ethyl;

or

R(35) is $C_1$–$C_9$-heteroaryl, which is unsubstituted or substituted by a substituent selected from the group consisting of F, Cl, $CF_3$, $CH_3$ and methoxy;

and the other substituents R(1), R(2) and R(3) in each case independently of one another are alkyl having 1, 2, 3 or 4 carbon atoms or phenyl, which is unsubstituted or substituted by a substituent selected from the group consisting of F, Cl, $CF_3$, methyl, methoxy, —$SO_2NR(17)R(8)$ and —$SO_2CH_3$;

R(17) and R(8) independently of one another are hydrogen, methyl or ethyl;

or

R(1) is hydrogen or alkyl having 1, 2, 3 or 4 carbon atoms; or R(3) is hydrogen;

R(4) is hydrogen or alkyl having 1, 2, 3 or 4 carbon atoms; and their pharmaceutically tolerable salts.

The designated alkyl radicals can be either straight-chain or branched.

($C_1$–$C_9$)-Heteroaryl is understood as meaning radicals which are derived from phenyl or naphthyl, in which one or more CH groups are replaced by N and/or in which at least two adjacent CH groups (with formation of a five-membered aromatic ring) are replaced by S, NH or O. In addition, one or both atoms of the condensation site of bicyclic radicals (as in indolizinyl) can also be N atoms.

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

If one of the substituents R(1) to R(4) contains one or more centers of asymmetry, these can be present independently of one another in either the S or R configuration. The compounds can be present as optical isomers, as diastereomers, as racemates or as mixtures thereof.

The designated alkyl radicals can be either straight-chain or branched.

The invention furthermore relates to a process for the preparation of the compounds I, which comprises reacting compounds of the formula II

HS—R(2)' II in which R(2)' is an optionally suitably protected radical R(2), with a monochloro- or monobromoamine prepared in situ according to generally known processes. This reaction is carried out in an inert solvent such as $CH_2Cl_2$, $CHCl_3$ or $CCl_4$ at a temperature between RT and the melting point of the solvent used, preferably between 0° C. and –40° C. In some cases, the amine on which the haloamine is based or alternatively water can also be employed as a solvent. Sulfonimidamides of the formula III

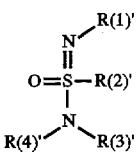 III are obtained in which R(1)', R(2)', R(3)' and R(4)' are optionally suitably protected or temporary radicals R(1), R(2), R(3) and R(4). Subsequent introduction of a radical R(3) can be carried out by means of aromatic nucleophilic substitutions, which are generally known for the sulfonamides analogous to the sulfonimidamides of the formula III.

The benzoic acid function is guanylated by methods which are known in principle by substituting a readily nucleophilically removable leaving group L in the compound IV

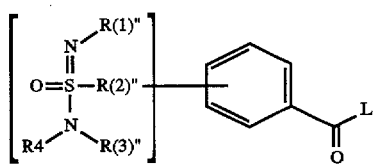 IV in which at least one of the substituents R(1"), R(2") or R(3") are defined as R(1), R(2) and R(3), but which instead of the guanidine group carries an easily removable leaving group L, by guanidine.

The introduction of the benzoic acid derivatives substituted in the phenyl moiety by sulfur, oxygen or nitrogen nucleophiles is carried out by methods of nucleophilic substitution in aromatics known from the literature. Leaving groups on the benzoic acid derivative which have proven suitable in this substitution are halides and trifluoromethanesulfonates. The reaction is advantageously carried out in a dipolar aprotic solvent, such as DMF or TMU, at a temperature from 0° C. up to the boiling point of the solvent, preferably from 80° C. up to the boiling point of the solvent. The acid scavenger used is advantageously an alkali metal or alkaline earth metal salt with an anion of high basicity and low nucleophilicity, for example $K_2CO_3$ or $CsCO_3$. Functional groups in the radicals R(1) to R(4), which can function as reductants, are advantageously synthesized after the introduction of the sulfonimidamide group. The demands on the protective groups during the preparation of the sulfonimidamide functionality are derived from the type of reaction. In this case, the reaction is an oxidation using a strong oxidant. Nitrogen-containing heteroaromatics, such as, for example, pyridinyl groups, can be protected in the form of the corresponding N-oxides.

The oxidation of the nitrogen in the heteroaryl substituent is carried out on suitable intermediate compounds such as the benzoic acid ester using methods known in principle. For example, m-chloroperbenzoic acid in an inert solvent such as methylene chloride at a temperature between −30° C. and the boiling point of the solvent has proven suitable. Methods for the reduction of heteroaryl N-oxides such as, for example, pyridine N-oxides are likewise known in principle. For example, the reaction with triphenylphosphine or trimethyl phosphite has proven suitable (C. Kaneko, A. Yamamoto, M. Gomi Heterocycles 12, 227 (1979)).

The alkyl or aryl substituents are introduced by methods known from the literature for the palladium-mediated cross-coupling of aryl halides with, for example, organozinc compounds, organostannanes, organoboronic acids or organoboranes.

In general, sulfonimidamides I are weak bases and can bind acid with formation of salts. Possible acid addition salts are salts of all pharmacologically tolerable acids, for example halides, in particular hydrochlorides, ascorbates, lactates, sulfates, citrates, tartrates, acetates, phosphates, methylsulfonates and p-toluenesulfonates.

U.S. Pat. No. 5,091,394 (HOE 89/F 288) and European Offenlegungsschrift 0 556 674 (HOE 92/F 034) describe benzoylguanidines in which, however, the substituents do not have the meanings claimed according to the present invention. No benzenesulfonimidamide derivatives are described. Additionally, the water solubility of these known benzoylguanidines leaves something to be desired.

On account of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the pathophysiological processes in the formation of ischemically induced damage, in particular in the triggering of ischemically induced cardiac arrythmias. Because of their protective actions against pathological hypoxic and ischemic situations, the compounds of the formula I according to the invention can be used, as a result of inhibition of the cellular $Na^+/H^+$ exchange mechanism, as pharmaceuticals for the treatment of all acute or chronic damage caused by ischemia or illnesses primarily or secondarily induced thereby. This relates to their use as medicaments for surgical interventions, e.g. in organ transplantation, where the compounds can be used both for the protection of the organs in the donor before and during removal, for the protection of removed organs, for example during treatment with or storage thereof in physiological bath fluids, and also during transfer to the recipient's body. The compounds are also useful pharmaceuticals having a protective action when carrying out angioplastic surgical interventions, for example on the heart and also on peripheral vessels. In accordance with their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and bacterial shock.

The compounds of the formula I according to the invention are moreover distinguished by potent inhibitory action on the proliferation of cells, for example fibroblast cell proliferation and the proliferation of vascular smooth muscle cells. The compounds of the formula I are therefore suitable as useful therapeutics for illnesses in which cell proliferation is a primary or secondary cause, and can therefore be used as antiatherosclerotics, agents against diabetic late complications, carcinomatous disorders, fibrotic disorders such as pulmonary fibrosis, fibrosis of the liver or fibrosis of the kidney, organ hypertrophies and hyperplasias, in particular in prostate hyperplasia or prostate hypertrophy.

The compounds according to the invention are effective inhibitors of the cellular sodium-proton antiporter ($Na^+/H^+$ exchanger), which is raised in numerous disorders (essential hypertension, atherosclerosis, diabetes etc.) even in those cells which are easily accessible to measurement, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative disorders etc. The compounds of the formula I are moreover suitable for preventive therapy for the prevention of the genesis of high blood pressure, for example of essential hypertension.

Compared with most known compounds, the compounds according to the invention have a significantly improved water solubility. They are therefore significantly better suited to i.v. administration.

Compared with the known readily water-soluble compounds, the compounds according to the invention are distinguished by their excellent bioavailability and pharmacokinetics.

Pharmaceuticals which contain a compound I can be administered orally, parenterally, intravenously, rectally or by inhalation, the preferred type of administration being dependent on the particular clinical picture of the disorder. The compounds I can be used here on their own or together with pharmaceutical auxiliaries, for example in veterinary and also in human medicine.

On the basis of his expert knowledge, the person skilled in the art is familiar with auxiliaries which are suitable for the desired pharmaceutical formulation. Beside solvents, gelling agents, suppository bases, tablet auxiliaries and other active compound excipients, antioxidants, dispersants, emulsifiers, antifoams, flavor corrigents, preservatives, solubilizers or colorants, for example, can be used.

For a form for oral administration, the active compounds are mixed with the additives suitable for this purpose, such as excipients, stabilizers or inert diluents and brought by the customary methods into the suitable administration forms, such as tablets, coated tablets, hard gelatin capsules, aqueous, alcoholic or oily solutions. Inert excipients which can be used are, for example, gum arabic, magnesia, magnesium carbonate, potassium phosphate, lactose, glucose or starch, in particular corn starch. Preparation can in this case take place either as dry or as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired with the substances customary for this purpose, such as solubilizers, emulsifiers or other auxiliaries. Possible solvents are, for example: water, physiological saline solution or alcohols, e.g. ethanol, propanol, glycerol, additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation can also contain still other pharmaceutical auxiliaries such as surfactants, emulsifiers and stabilizers, as well as a propellant. Such a preparation customarily contains the active compound in a concentration from approximately 0.1 to 10, in particular from approximately 0.3 to 3% by weight.

The dose of the active compound of the formula I to be administered and the frequency of administration depend on the potency and duration of action of the compounds used; additionally also on the nature and severity of the illness to be treated and on the sex, age, weight and individual responsiveness of the mammal to be treated.

On average, the daily dose of a compound of the formula I in the case of a patient of weight approximately 75 kg is at least 0.001 mg/kg of body weight, preferably at least 0.01 mg/kg of body weight, up to at most 10 mg/kg of body weight, preferably to at most 1 mg/kg of body weight. In acute episodes of the illness, for example immediately after suffering a cardiac infarct, still higher and especially more frequent doses may also be necessary, e.g. up to 4 individual doses per day. In particular when administered i.v., for example in the case of an infarct patient in the intensive care unit, up to 100 mg per day may be necessary.

| AIBN | α,α-azobisisobutyronitrile |
|---|---|
| Bn | benzyl |
| Brine | saturated aqueous NaCl solution |
| $CH_2Cl_2$ | dichloromethane |
| DCI | desorption chemical ionization |
| DIP | diisopropyl ether |
| DMA | dimethylacetamide |
| DME | dimethoxyethane |
| DMF | N,N-dimethylformamide |
| EA | ethyl aceate (EtOAc) |
| EI | electron impact |
| eq | equivalent |
| ES | electrospray ionization |
| Et | ethyl |
| FAB | fast atom bombardment |
| HEP | n-heptane |
| HOAc | acetic acid |
| Me | methyl |

-continued

| MeOH | methanol |
|---|---|
| mp | melting point |
| MTP | methyl tertiary-butyl ether |
| NBS | N-bromosuccinimide |
| NMP | N-methylpyrrolidone |
| RT | room temperature |
| THF | tetrahydrofuran |
| TMU | N,N,N',N'-tetramethylurea |
| Tol | Toluene |
| CNS | central nervous system |

Experimental section General procedure for the preparation of benzoylguanidines (I) Variant A: from benzoic acids (II, L=OH)

0.01M of the benzoic acid derivative of the formula II is dissolved or suspended in 60 ml of anhydrous THF and then treated with 1.78 g (0.011M) of carbonyldiimidazole. After stirring for 2 hours at RT, 2.95 g (0.05M) of guanidine are introduced into the reaction solution. After stirring overnight, the THF is distilled off under reduced pressure (rotary evaporator), the residue is treated with water, the mixture is adjusted to pH 6 to 7 with 2N HCl and the corresponding benzoylguanidine (formula I) is filtered off. The benzoylguanidines thus obtained can be converted into the corresponding salts by treating with aqueous, methanolic or etherieal hydrochloric acid or other pharmacologically tolerable acids.

General procedure for the preparation of benzoylguanidines (I) Variant B: from alkyl benzoates (II, L=O-alkyl)

5 mmol of the alkyl benzoate of the formula II and 25 mmol of guanidine (free base) are dissolved in 15 ml of isopropanol or suspended in 15 ml of THF and boiled under reflux (typical reaction time 2 to 5 h) until conversion is complete (thin-layer checking). The solvent is distilled off under reduced pressure (rotary evaporator), the residue is taken up in 300 ml of EA and the solution is washed 3 times using 50 ml of $NaHCO_3$ solution each time. It is dried over $Na_2SO_4$, the solvent is distilled off in vacuo and the residue is chromatographed on silica gel using a suitable eluent, e.g. EA/MeOH 5:1. (For salt formation compare Variant A)

Example 1: 4-(4-Fluorobenzene-N,N'-diethylsulfimidamoyl)-3-methyl-sulfonylbenzoylguanidine, dihydrochloride

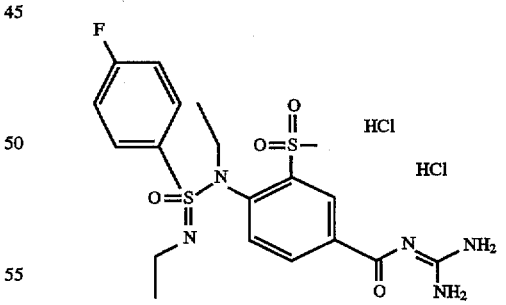

a. 4-Fluorobenzenesulfonic acid N,N'-diethylimidamide 146 ml of a 70% aqueous ethylamine solution are treated at −30° C. with 30.8 ml of bromine. The mixture is allowed to warm to −5° C., then 19.2 ml of 4-fluorothiophenol are added dropwise and the mixture is subsequently stirred at RT for 5 h. The reaction solution is then first treated with 100 ml of a saturated aqueous $Na_2SO_3$ solution, then with 200 ml of a saturated aqueous $Na_2CO_3$ solution and extracted 5 times with 200 ml of EA each time. The organic phase is dried over $Na_2SO_4$, the solvent is removed in vacuo, and the residue is chromatographed on silica gel using EA/Tol/MeOH 5:5:2. 1.8 g of a colorless oil are obtained. $R_f$ (EA/Tol/MeOH 5:5:2)=0.68 MS (ES): 231 (M+H)$^+$ b. 5-Carboxy-2-fluorobenzenesulfinic acid 15.6 g (0.124 mol) of sodium sulfite are dissolved in 120 ml of water at 70° C. While maintaining the temperature, 23.8 g (0.1 mol) of 4-fluoro-3-chlorosulfonylbenzoic acid and 10N NaOH are added simultaneously and in portions such that the pH is kept between 9 and 10 (exothermic reaction). The mixture is stirred for a further 3 hours at 70° C., stirred for a further 15 minutes with active carbon and then filtered. The filtrate is adjusted to pH 0–1 using concentrated hydrochloric acid with external cooling and the crystalline 5-carboxy-2-fluorobenzenesulfinic acid is filtered off.

Colorless crystals, m.p.: 167°–170° C.

c. Disodium 5-carboxy-2-fluorobenzenesulfinate:

obtained by introducing 17.2 g (0.084 mol) of 5-carboxy-2-fluorobenzenesulfinic acid into a stirred solution of 6.72 g (0.168 mol) of NaOH in a mixture of 150 ml of methanol and 30 ml of water: after filtration of suspended matter, the solvent is distilled off and the residue is crystallized with acetone. Colorless crystalline substance, m.p.: >320° C.

d. Methyl 4-fluoro-3-methylsulfonylbenzoate:

30 g (0.21 mol) of methyl iodide are added to a suspension of 15 g (0.06 mol) of disodium 5-carboxy-2-fluorobenzenesulfinate in 80 ml of dry DMF, the mixture is stirred for 6 hours at 60° C., the solvent is distilled off and the residue is treated with water. The mixture is stirred for 30 min with ice-cooling and the precipitate is filtered off. Colorless crystalline substance, m.p.: 102°–105° C.

e. Methyl 4-(4-fluorobenzene-N,N'-diethylsulfimidamoyl)-3-methylsulfonylbenzoate 461 mg of 4-fluorobenzenesulfonic acid N,N'-diethylimidamide and 464 mg of methyl 4-fluoro-3-trifluoromethylbenzoate are dissolved in 10 ml of NMP, 2.0 g of CS$_2$CO$_3$ are added and the mixture is stirred at 100° C. for 3 h. After cooling, the reaction mixture is diluted with 300 ml of EA and washed 3 times with 100 ml of water each time. It is dried over Na$_2$SO$_4$ and the residue is chromatographed on silica gel using DIP. 440 mg of a colorless oil are obtained. $R_f$ (DIP)=0.27 MS (FAB): 443 (M+H)$^+$ f. 4-(4-Fluorobenzene-N,N'-diethylsulfimidamoyl)-3-methylsulfonylbenzoylguanidine, dihydrochloride 180 mg of methyl 4-(4-fluorobenzene-N,N'-diethylsulfimidamoyl)-3-methylsulfonylbenzoate are reacted according to the general procedure for the preparation of benzoylguanidines, Variant B. 140 mg of a colorless oil are obtained, which is converted into the dihydrochloride using aqueous HCl solution. m.p. (dihydrochloride)=193° C. (decomposition) $R_f$ (EA)=0.31 MS (ES): 470 (M+H)$^+$ The title compound of Example 2 was prepared from methyl 4-fluoro-3-trifluoromethylbenzoate analogously to Example 1:

Example 2: 4-(4-Fluorobenzene-N,N'-diethylsulfimidamoyl)-3-trifluoro-methylbenzoylguanidine, dihydrochloride

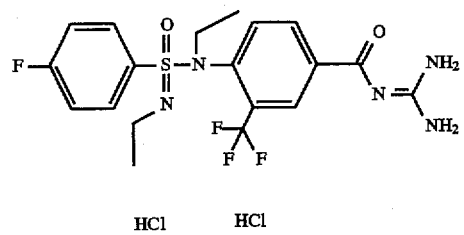

amorphous solid without defined melting point. $R_f$ (EA)= 0.51 MS (ES): 460 (M+H)$^+$ a) Methyl 4-fluoro-3-trifluoromethylbenzoate 5 g of 4-fluoro-3-trifluoromethylbenzoic acid and 9 ml of SOCl$_2$ are stirred at 60° C. for 8 h in 50 ml of MeOH. The volatile constituents are then removed in vacuo and 5.1 g of a colorless oil are obtained, which is further employed without purification. Rf (EA/MeOH 10:1)=0.74 MS (DCI) 223 (M+H)$^+$ Example 3: 3-Methylsulfonyl-4-(4-fluorobenzenesulfimidamoyl)benzoylguanidine a) 4-Fluorobenzenesulfonic acid N,N'-bis-t-butylimidamide 100 ml of t-butylamine and 30 ml of water are cooled to −30° C., and at this temperature 6.2 ml of bromine are added dropwise. The mixture is stirred at this temperature for 30 minutes. Then it is warmed to −5° C. and 4.6 g of 4-fluorothiophenol are added dropwise. The mixture is allowed to warm to RT and is stirred at this temperature for 10 h. The reaction mixture is stirred into 200 ml of saturated aqueous Na$_2$SO$_3$ solution, 200 ml of saturated aqueous Na$_2$CO$_3$ solution are added and the mixture is stirred for 30 minutes. It is extracted 4 times using 150 ml of EA each time, the organic phase is dried over Na$_2$SO$_4$ and the solvent is removed in vacuo. The residue is taken up using 200 ml of aqueous 1N HCl solution, the solution is stirred for 1 hour, then it is adjusted to pH=9 using Na$_2$CO$_3$ and extracted 3 times using 150 ml of EA each time. It is dried over Na$_2$SO$_4$ and the solvent is removed in vacuo. The residue is chromatographed on silica gel using EA/HEP 1:2. 3.2 g of a colorless oil are obtained. $R_f$ (DIP)=0.40 MS (ES):287 (M+H)$^+$ b) 4-Fluorobenzenesulfonimidamide 3.1 g of 4-fluorobenzenesulfonic acid N,N'-bis-t-butylimidamide are dissolved in 55 ml of a 33% solution of HBr in glacial acetic acid and the solution is stirred at RT for 10 hours. The reaction mixture is slowly stirred into 400 ml of a saturated aqueous Na$_2$CO$_3$ solution and extracted 4 times using 150 ml of EA. The organic phase is dried over Na$_2$SO$_4$ and the solvent is removed in vacuo. Chromatography on silica gel using MTB yields 1.4 g of colorless crystals m.p. 111° C. $R_f$ (EA/MeOH 10:1)=0.44 MS (ES): 175 (M+H)$^+$ c) Methyl 3-methylsulfonyl-4-(4-fluorobenzenesulfimidamoyl)benzoate 350 mg of 4-fluorobenzenesulfonimidamide, 460 mg of methyl 4-fluoro-3-methylsulfonylbenzoate and 1.96 g of $Cs_2CO_3$ are dissolved in 10 ml of NMP and the solution is stirred at 100° C. for 4 hours. The reaction mixture is then stirred into 100 ml of a saturated aqueous $NaHCO_3$ solution, extracted 3 times with 100 ml of EA each time and the organic phase is washed 3 times with 50 ml of water each time. It is dried over $Na_2SO_4$ and the solvent is removed in vacuo. Chromatography on silica gel using MTB yields 130 mg of a colorless oil. $R_f$(MTB)=0.58 MS (ES): 387 (M+H)$^+$ d) 3-Methylsulfonyl-4-(4-fluorobenzenesulfimidamoyl) benzoylguanidine 120 mg of methyl 3-methylsulfonyl-4-(4-fluorobenzenesulfimidamoyl)benzoate are guanylated according to the general procedure for the preparation of benzoylguanidines, Variant B, using 90 mg of guanidine in 1 ml of isopropanol. Reaction time 3 hours under reflux. Chromatography on silica gel using EA/MeOH 5:1 yields 70 mg of a colorless oil. Melting point of the dihydrochloride: 240° C. $R_f$(EA/MeOH 5:1)=0.14 MS (ES): 414 (M+H)$^+$ Example 4: 2-isopropyl-5-guanidinocarbonylbenzenesulfonic acid N,N'-dimethylimidamide

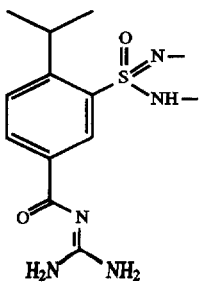

a) 2-isopropylbenzenesulfonic acid N,N'-dimethylimidamide 110 ml of a 40% aqueous solution of methylamine are treated with 5.7 ml of bromine at −30° C. The mixture is stirred at this temperature for 30 minutes, then it is warmed to −5° C., and 5.0 ml of 2-isopropylthiophenol are added dropwise. The reaction mixture is stirred at RT for 5 hours, then it is stirred into 200 ml of a saturated aqueous $Na_2SO_3$ solution. 200 ml of a saturated aqueous $Na_2CO_3$ solution are added and the mixture is stirred at RT for 1 hour. It is then extracted 3 times using 150 ml of EA each time. The organic phase is dried over $Na_2SO_4$ and the solvent is removed in vacuo. Chromatography on silica gel using EA yields 2.8 g of a colorless solid, m.p. 84°–85° C. $R_f$(EA)=0.48 MS (ES): 227 (M+H)$^+$ b) 2-isopropyl-5-iodobenzenesulfonic acid N,N'-dimethylimidamide 2.7 g of 2-isopropylbenzenesulfonic acid N,N'-dimethylimidamide are dissolved in 10 ml of $CF_3SO_3H$, then 2.7 g of N-iodosuccinimide are added, and the solution is stirred at RT for 4 hours. The reaction mixture is slowly added dropwise to a mixture of 150 ml of saturated aqueous $NaHCO_3$ solution and 150 ml of saturated aqueous $Na_2CO_3$ solution. It is extracted 3 times using 150 ml of EA each time, the organic phase is dried over $Na_2SO_4$ and the solvent is removed in vacuo. Chromatography on silica gel using MTB yields 3.6 g of a colorless oil. $R_f$(MTB)=0.51 MS (ES): 353 (M+H)$^+$ c) 2-isopropyl-5-n-butoxycarbonylbenzenesulfonic acid N,N'-dimethylimidamide 3.6 g of 2-isopropyl-5-iodobenzenesulfonic acid N,N'-dimethylimidamide, 37.6 mg of Pd(II) acetate, 69.2 mg of 1,3-bis(diphenylphosphino)propane and 5.1 ml of tri-n-butylamine are dissolved in 11 ml of n-butanol and 22 ml of DMF and the solution is stirred at 100° C. for 6 hours. The reaction mixture is taken up in 250 ml of saturated aqueous $NaHCO_3$ solution, 100 ml of water are added and the mixture is extracted 3 times using 150 ml of EA each time. The organic phase is dried over $Na_2SO_4$ and the solvent is removed in vacuo. Chromatography on silica gel using EN/HEP 1:1 yields 340 mg of a colorless oil. $R_f$ (EA/HEP 1:1)=0.21 MS (ES): 327 (M+H)$^+$ d) 2-isopropyl-5-guanidinocarbonylbenzenesulfonic acid N,N'-dimethylimidamide 177 mg of guanidine hydrochloride are dissolved in 2.5 ml of DMF and a solution of 190 mg of potassium t-butoxide in 2.5 ml of DMF is added. The mixture is stirred at RT for 1 hour, then a solution of 110 mg of 2-isopropyl-5-n-butoxycarbonylbenzenesulfonic acid N,N'-dimethylimidamide in 5 ml of DMF is added. The reaction mixture is stirred at RT for 24 hours, stirred into 100 ml of a saturated aqueous $NaHCO_3$ solution, and extracted 3 times using 100 ml of EA each time. The organic phase is dried over $Na_2SO_4$ and the solvent is removed in vacuo. Chromatography on silica gel using EA/MeOH 1:8 yields 32 mg of a white solid, m.p. 148° C. (with decomposition). $R_f$ (EA/MeOH 1:8)=0.21 MS (ES): 312 (M+H)$^+$ Pharmacological data:

Inhibition of the Na$^+$/H$^+$ exchanger of rabbit erythrocytes

White New Zealand rabbits (Ivanovas) received a standard diet with 2% cholesterol for six weeks in order to activate Na$^+$/H$^+$ exchange and thus to be able to determine the Na$^+$ influx into the erythrocytes via Na$^+$/H$^+$ exchange by flame photometry. The blood was taken from the ear arteries and rendered incoagulable by means of 25 IU of potassium heparin. A part of each sample was used for the duplicate determination of the hematocrit by centrifugation. Aliquots of 100 µl in each case were used to measure the Na$^+$ starting content of the erythrocytes.

In order to determine the amiloride-sensitive sodium influx, 100 µl of each blood sample were incubated in each case in 5 ml of a hyperosmolar salt-sucrose medium (mmol/l: 140 NaCl, 3 KCl, 150 sucrose, 0.1 ouabain, 20 tris-hydroxymethylaminomethane) at pH 7.4 and 37° C. The erythrocytes were then washed three times with ice-cold $MgCl_2$ ouabain solution (mmol/l: 112 $MgCl_2$, 0.1 ouabain) and hemolyzed in 2.0 ml of distilled water. The intracellular sodium content was determined by flame photometry.

The net Na$^+$ influx was calculated from the difference between sodium starting values and the sodium content of the erythrocytes after incubation. The amiloride-inhibitable sodium influx resulted from the difference between the sodium content of the erythrocytes after incubation with and without amiloride 3×10$^{-4}$ mol/l. This procedure was also used in the case of the compounds according to the invention.

Results Inhibition of the Na$^+$/H$^+$ exchanger:

| Example | IC$_{50}$ (mmol/l) |
| --- | --- |
| 1 | 0.68 |
| 2 | 0.053 |
| 3 | 2 |
| 4 | 6 |

What is claimed is:

1. A sulfonimidamide of the formula I

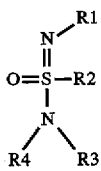

in which:

at least one of the three substituents R(1), R(2) and R(3) is a benzoylguanidine

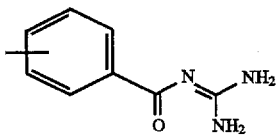

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, $-(CH_2)_m-R(14)$, F, Cl, Br, I, $-C\equiv N$, $CF_3$, $R(22)SO_2-$, $R(23)R(24)N-CO-$, $R(25)-CO-$, $R(26)R(27)N-SO_2$, $-OR(35)$, $-SR(35)$ or $-NR(35)R(36)$;

m is zero, 1 or 2;

R(14) is $-(C_3-C_8)$-cycloalkyl or phenyl, which is unsubstituted or substituted by 1–3 substituents selected from the group consisting of F and Cl, $-CF_3$, methyl, methoxy and $-NR(15)R(16)$;

R(15) and R(16) independently of one another are hydrogen or $-CH_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, $(CH_2)_nR(29)$ or $-CF_3$;

n is zero, 1, 2, 3 or 4;

R(29) is $-(C_3-C_7)$-cycloalkyl or phenyl, which is unsubstituted or substituted by 1–3 substituents selected from the group consisting of F, Cl, $-CF_3$, methyl, methoxy and $-NR(30)R(31)$;

R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24) and also R(26) and R(27) together are 5 or 6 methylene groups, of which a $CH_2$ group can be replaced by oxygen, $-S-$, $-NH-$, $-NCH_3$ or $-N$-benzyl;

R(35) and R(36) independently of one another are hydrogen or alkyl having 1, 2, 3, 4, 5 or 6 carbon atoms;

or

R(35) and R(36) together are 4–7 methylene groups, of which a $CH_2$ group can be replaced by oxygen, $-S-$, $-NH-$, $-NCH_3$ or $-N$-benzyl;

or

R(35) is phenyl, which is unsubstituted or substituted by 1–3 substituents selected from the group consisting of F, Cl, $-CF_3$, methyl, methoxy, $SO_2R(5)$, $SO_2NR(6)R(7)$ and $-NR(32)R(33)$;

R(5) is alkyl having 1, 2, 3, 4, 5 or 6 carbon atoms R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms;

or

R(35) is $C_1$–$C_9$-heteroaryl, which is unsubstituted or substituted by 1–3 substituents selected from the group consisting of F, Cl, $CF_3$, $CH_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, $(CH_2)_pR(10)$ p is zero, 1, 2, 3 or 4;

R(10) is phenyl, which is unsubstituted or substituted by 1–3 substituents selected from the group consisting of F, Cl, $-CF_3$, methyl, methoxy, $-SO_2NR(17)R(8)$ and $-SO_2R(9)$;

R(17) and R(8) independently of one another are hydrogen or alkyl having 1, 2, 3 or 4 carbon atoms;

R(9) is alkyl having 1, 2, 3 or 4 carbon atoms;

or the other radical R(1) and R(3) in each case is hydrogen,

R(4) is hydrogen or alkyl having 1, 2, 3 or 4 carbon atoms; or its pharmaceutically tolerable salts.

2. A compound of the formula I as claimed in claim 1, in which: one of the substituents R(1), R(2) and R(3) is a benzoylguanidine

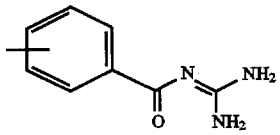

which is unsubstituted or substituted in the phenyl moiety by 1–3 substituents selected from the group consisting of alkyl having 1, 2, 3 or 4 carbon atoms, alkenyl having 2, 3 or 4 carbon atoms, $-(CH_2)_m R(14)$, F, Cl, $CF_3$, $R(22)SO_2-$, $R(23)R(24)N-CO-$, $R(25)-CO-$, $R(26)R(27)N-SO_2$, $-OR(35)$, $-SR(35)$ and $-NR(35)R(36)$;

R(22) and R(25) independently of one another are methyl or $-CF_3$;

R(23), R(24), R(26) and R(27) independently of one another are hydrogen or methyl;

m is zero, 1 or 2;

R(14) is $-(C_3-C_6)$-cycloalkyl or phenyl, which is unsubstituted or substituted by 1–2 substituents selected from the group consisting of F and Cl, $-CF_3$, methyl and methoxy;

R(35) and R(36) independently of one another are hydrogen or alkyl having 1, 2, 3 or 4 carbon atoms;

or

R(35) and R(36) together are 4–6 methylene groups, of which a $CH_2$ group can be replaced by oxygen, $-S-$, $-NH-$ or $-NCH_3$;

or

R(35) is phenyl, which is unsubstituted or substituted by 1–2 substituents selected from the group consisting of F, Cl, $-CF_3$, methyl, methoxy, $SO_2R(5)$ and $SO_2NR(6)R(7)$;

R(5) is alkyl having 1, 2, 3 or 4 carbon atoms R(6) and R(7) independently of one another are hydrogen, methyl or ethyl;

or

R(35) is $C_1$–$C_9$-heteroaryl, which is unsubstituted or substituted by 1–2 substituents selected from the group consisting of F, Cl, $CF_3$, $CH_3$ and methoxy;

and the other substituents R(1), R(2) and R(3) in each case independently of one another are alkyl having 1, 2, 3, 4, 5 or 6 carbon atoms or $(CH_2)_pR(10)$;

p is zero, 1 or 2;

R(10) is phenyl, which is unsubstituted or substituted by 1–2 substituents selected from the group consisting of F, Cl, $CF_3$, methyl, methoxy, —$SO_2NR(17)R(8)$ and —$SO_2R(9)$;

R(17) and R(8) independently of one another are hydrogen, methyl or ethyl;

R(9) is methyl or ethyl;

or the other substituent R(1) and R(3) in each case is hydrogen;

R(4) is hydrogen or alkyl having 1, 2, 3 or 4 carbon atoms.

3. A compound of the formula I as claimed in claim 1, in which: one of the substituents R(1), R(2) and R(3) is a benzoylguanidine

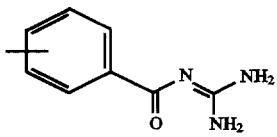

which is unsubstituted or substituted in the phenyl moiety by 1–2 radicals selected from the group consisting of alkyl having 1, 2, 3 or 4 carbon atoms, R(14), F, Cl, $CF_3$, $R(22)SO_2$—, $R(23)R(24)N$—CO—, $R(25)$—CO—, $R(26)R(27)N$—$SO_2$, —OR(35), —SR(35) and —NR(35)R(36);

R(22) and R(25) independently of one another are methyl or $CF_3$;

R(23), R(24), R(26) and R(27) independently of one another are hydrogen or methyl;

R(14) is —($C_3$–$C_6$)-cycloalkyl or phenyl, which is unsubstituted or substituted by a substituent selected from the group consisting of F and Cl, —$CF_3$, methyl and methoxy;

R(35) and R(36) independently of one another are hydrogen or alkyl having 1, 2, 3 or 4 carbon atoms;

or

R(35) is phenyl, which is unsubstituted or substituted by a substituent selected from the group consisting of F, Cl, —$CF_3$, methyl, methoxy, $SO_2CH_3$ and $SO_2NR(6)R(7)$;

R(6) and R(7) independently of one another are hydrogen, methyl or ethyl;

or

R(35) is $C_1$–$C_9$-heteroaryl, which is unsubstituted or substituted by a substituent selected from the group consisting of F, Cl, $CF_3$, $CH_3$ and methoxy;

and the other substituents R(1), R(2) and R(3) in each case independently of one another are alkyl having 1, 2, 3 or 4 carbon atoms or phenyl, which is unsubstituted or substituted by a substituent selected from the group consisting of F, Cl, $CF_3$, methyl, methoxy, —$SO_2NR(17)R(8)$ and —$SO_2CH_3$;

R(17) and R(8) independently of one another are hydrogen, methyl or ethyl;

or

R(1) is hydrogen or alkyl having 1, 2, 3 or 4 carbon atoms;

or

R(3) is hydrogen,

R(4) is hydrogen or alkyl having 1, 2, 3 or 4 carbon atoms.

4. A compound I as claimed in claim 1, selected from the group comprising 2-isopropyl-5-guanidinocarbonylbenzenesulfonic acid N,N'-dimethylimidamide; 4-(4-fluorobenzene-N,N'-diethylsulfimidamoyl)-3-methylsulfonylbenzoylguanidine, dihydrochloride; 4-(4-fluorobenzene-N,N'-diethylsulfimidamoyl)-3-trifluoromethylbenzoylguanidine dihydrochloride; and 3-methylsulfonyl-4-(4-fluorobenzenesulfimidamoyl)benzoylguanidine.

5. A pharmaceutical composition comprising an effective amount for use as a pharmaceutical of a compound of the formula I as claimed in claim 1 together with a pharmaceutically acceptable carrier.

6. A method for the treatment of arrythmias which comprises administering to a mammal in need of such treatment a pharmaceutical composition as set forth in claim 5.

7. A method for the treatment of arrythmias with comprises admininstering to a mammal in need of such treatment an effective amount of a compound I as set forth in claim 1.

8. A method for the treatment or prophylaxis of cardiac infarct which comprises administering to a mammal in need of such treatment or prophylaxis a pharmaceutical composition as set forth in claim 5.

9. A method for the treatment or prophylaxis of cardiac infarct which comprises administering to a mammal in need of such treatment or prophylaxis an effective amount of a compound I as set forth in claim 1.

10. A method for the treatment or prophylaxis of angina pectoris which comprises administering to a mammal in need of such treatment or prophylaxis a pharmaceutical composition as set forth in claim 5.

11. A method for the treatment or prophylaxis of cardiac infarct which comprises administering to a mammal in need of such treatment or prophylaxis an effective amount of a compound I as set forth in claim 1.

12. A method for the treatment or prophylaxis of ischemic conditions of the heart which comprises administering to a mammal in need of such treatment or prophylaxis a pharmaceutical composition as set forth in claim 5.

13. A method for the treatment or prophylaxis of ischemic conditions of the heart which comprises administering to a mammal in need of such treatment or prophylaxis an effective amount of a compound I as set forth in claim 1.

14. A method for the treatment or prophylaxis of ischemic conditions of the peripheral and central nervous system and of stroke which comprises administering to a mammal in need of such treatment or prophylaxis a pharmaceutical composition as set forth in claim 5.

15. A method for the treatment or prophylaxis of ischemic conditions of the peripheral and central nervous system and of stroke which comprises administering to a mammal in need of such treatment or prophylaxis an effective amount of a compound I as set forth in claim 1.

16. A method for the treatment or prophylaxis of ischemic conditions of the peripheral organs and members which comprises administering to a mammal in need of such treatment or prophylaxis a pharmaceutical composition as set forth in claim 5.

17. A method for the treatment or prophylaxis of ischemic conditions of the peripheral organs and members which comprises administering to a mammal in need of such treatment or prophylaxis an effective amount of a compound I as set forth in claim 1.

18. A method for the treatment of states of shock comprising administering to a mammal in need of such treatment a pharmaceutical composition as set forth in claim 5.

19. A method for the treatment of states of shock which comprises administering to a mammal in need of such treatment an effective amount of a compound I as set forth in claim 1.

20. A method which comprises using a compound of the formula I as claimed in claim 1 in surgical operations and organ transplantation.

21. A method which comprises using a compound of the formula I as claimed in claim 1 for the preservation and storage of transplants for surgical measures.

22. A method for the treatment of diseases in which cell proliferation is a primary or secondary cause. which comprises administering to a mammal in need of such treatment a pharmaceutical composition as set forth in claim 5.

23. A method for the treatment of diseases in which cell proliferation is a primary or secondary cause which comprises administering to a mammal in need of such treatment an effective amount of a compound I as set forth in claim 1.

24. A method which comprises using a compound of the formula I as set forth in claim 1 to produce a scientific tool to inhibit Na+/H+ exchanger to diagnose hypertension and proliferative diseases.

25. A method as set forth in claim 22 wherein the diseases are atherosclerosis, late-onset diabetic complications, carcinomatous disorders, fibrotic disorders and prostate hyperplasia.

26. A method as set forth in claim 25 wherein the fibrotic disorders are pulmonary fibrosis, fibrosis of the liver or fibrosis of the kidney.

27. A method as set forth in claim 23 wherein the diseases are atherosclerosis, late-onset diabetic complications, carcinomatous disorders, fibrotic disorders and prostate hyperplasia.

28. A method as set forth in claim 27 wherein the fibrotic disorders are pulmonary fibrosis, fibrosis of the liver or fibrosis of the kidney.

\* \* \* \* \*